(12) United States Patent
Pillsbury (10) Patent No.: US 10,028,987 B1
(45) Date of Patent: Jul. 24, 2018

(54) CANNABIS-INFUSED MILK

(71) Applicant: Chocowaska Cooperative, Inc., Dos Rios, CA (US)

(72) Inventor: Dylan Pillsbury, Dos Rios, CA (US)

(73) Assignee: CHOCOWASKA COOPERATIVE, INC., Dos Rios, CA (US)

( * ) Notice: Subject to any disclaimer, the term of this patent is extended or adjusted under 35 U.S.C. 154(b) by 33 days.

(21) Appl. No.: 15/386,106

(22) Filed: Dec. 21, 2016

Related U.S. Application Data

(60) Provisional application No. 62/271,108, filed on Dec. 22, 2015.

(51) Int. Cl.
| | |
|---|---|
| *A61K 36/00* | (2006.01) |
| *A61K 36/185* | (2006.01) |
| *A61K 9/00* | (2006.01) |
| *A61K 31/352* | (2006.01) |
| *A61K 31/05* | (2006.01) |
| *A61K 31/192* | (2006.01) |
| *A23L 2/38* | (2006.01) |
| *A23L 2/56* | (2006.01) |

(52) U.S. Cl.
CPC .............. *A61K 36/185* (2013.01); *A23L 2/38* (2013.01); *A23L 2/56* (2013.01); *A61K 9/0095* (2013.01); *A61K 31/05* (2013.01); *A61K 31/192* (2013.01); *A61K 31/352* (2013.01); *A23V 2002/00* (2013.01)

(58) Field of Classification Search
CPC ....................................................... A61K 36/00
USPC .......................................................... 424/725
See application file for complete search history.

(56) References Cited

U.S. PATENT DOCUMENTS

2004/0049059 A1    3/2004  Mueller

FOREIGN PATENT DOCUMENTS

CN            102246995  A   * 11/2011

\* cited by examiner

*Primary Examiner* — Michael V Meller
(74) *Attorney, Agent, or Firm* — Kilpatrick Townsend & Stockton LLP (57) ABSTRACT

The present invention is directed to compositions and methods comprising a *cannabis*-infused milk. The milk can be used as an oral dosage form for pharmaceutical delivery of cannabinoids.

12 Claims, 5 Drawing Sheets

CANNABIS-INFUSED MILK

CROSS-REFERENCE TO RELATED APPLICATIONS

This application claims the benefit of U.S. Provisional Application No. 62/271,108 (filed Dec. 22, 2015). This application is incorporated by reference in its entirety for all purposes.

FIELD OF THE INVENTION

The present invention is directed to compositions and methods comprising a *cannabis*-infused milk. The milk can be used as an oral dosage form for pharmaceutical delivery of cannabinoids.

BACKGROUND OF THE INVENTION

The hemp, or *Cannabis*, plant has long been used as a natural source for the pharmaceutically active compound $\Delta^9$-tetrahydrocannabinol ($\Delta^9$-THC), which has both euphoric and therapeutic effects. Although $\Delta^9$-THC can be extracted and used in purified form, the *Cannabis* plant includes many other structurally related compounds, such as cannabidiol (CBD) and other cannabinoids, that can also contribute to the pharmaceutical effects of *cannabis*. See, e.g., U.S. Pat. App. Pub. No. US 2004/0049059. *Cannabis* plant derivatives, such as medical marijuana, have been used to treat pain, nausea, appetite loss, epileptic seizures, multiple sclerosis symptoms, and other disorders.

*Cannabis* is typically administered either by smoking, drinking (thorough a brewed beverage), eating, or inhaling through a vaporizer. Smoking *cannabis* provides quicker systemic effects, but its smoke may worsen or even cause respiratory conditions. Alternative, more palatable formulations would be advantageous, especially for younger patients.

The present invention satisfies these and other needs as shown in its specification and embodiments.

BRIEF SUMMARY OF THE INVENTION

In certain aspects, the present invention provides an alternative, palatable, and easily administered form of *cannabis*.

In certain aspects, the invention sets forth a method for preparing a *cannabis*-infused milk, wherein the method comprises, consists essentially of, or consists of:

heating a pre-mash mixture to form a mash, wherein the mash comprises *Cannabis* plant material, a milk, and an oil;

pressing the mash to form a pressate; and filtering the pressate to produce a *cannabis*-infused milk.

In some embodiments, the method further comprises pasteurizing the *cannabis*-infused milk or flavoring the *cannabis*-infused milk. In some embodiments, the composition is stirred in the same direction during heating.

In some embodiments, the *cannabis* is raw *cannabis*. In some embodiments, the milk does not contain lactose (e.g., hemp milk). In some embodiments, the oil is coconut oil.

In some embodiments, the pre-mash mixture is heated to about 200° F. In some embodiments, the pre-mash mixture is heated at least twice before the pressing.

In some embodiments, the pressing is through a nylon mesh. In some embodiments, the pressate so formed is filtered through a screen (e.g., an about 220 micron screen).

In certain aspects, the invention sets forth the *cannabis*-infused milk produced by a method described herein.

In certain aspects, the invention sets forth a pharmaceutical composition comprising, consisting essentially of, or consisting of *cannabis*-infused milk (e.g., as described herein).

In some embodiments, the pharmaceutical composition comprises a flavoring. In some embodiments, the flavoring is selected from chocolate, vanilla, strawberry, mocha, peppermint, black cherry, or coffee. These and other aspects, objects and embodiments will be more apparent when read with the detailed description and figures that follow.

DETAILED DESCRIPTION OF THE INVENTION

I. Definitions

The terms "a," "an," or "the" as used herein not only includes aspects with one member, but also includes aspects with more than one member. For example, an embodiment including "an oil and a flavoring agent" should be understood to present certain aspects with at least a second oil, at least a second flavoring agent, or both.

The term "about" as used herein to modify a numerical value indicates a defined range around that value. If "X" were the value, "about X" would generally indicate a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X."

When "about" is applied to the beginning of a numerical range, it applies to both ends of the range. Thus, "from about 1 to 10" is equivalent to "from about 1 to about 10." When "about" is applied to the first value of a set of values, it applies to all values in that set. Thus, "about 2, 5, or 11" is equivalent to "about 2, about 5, or about 11."

The term "*Cannabis*" is used herein to apply to the hemp plant, while "cannibis" is used herein to refer to agricultural products that are derived from the hemp plant (e.g., harvested *Cannabis* plant material).

"Formulation," "pharmaceutical composition," and "composition" as used interchangeably herein are equivalent terms referring to a composition of matter for pharmaceutical use.

The term "or" as used herein should in general be construed non-exclusively. For example, an embodiment of "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

II. Embodiments

Figure 1:
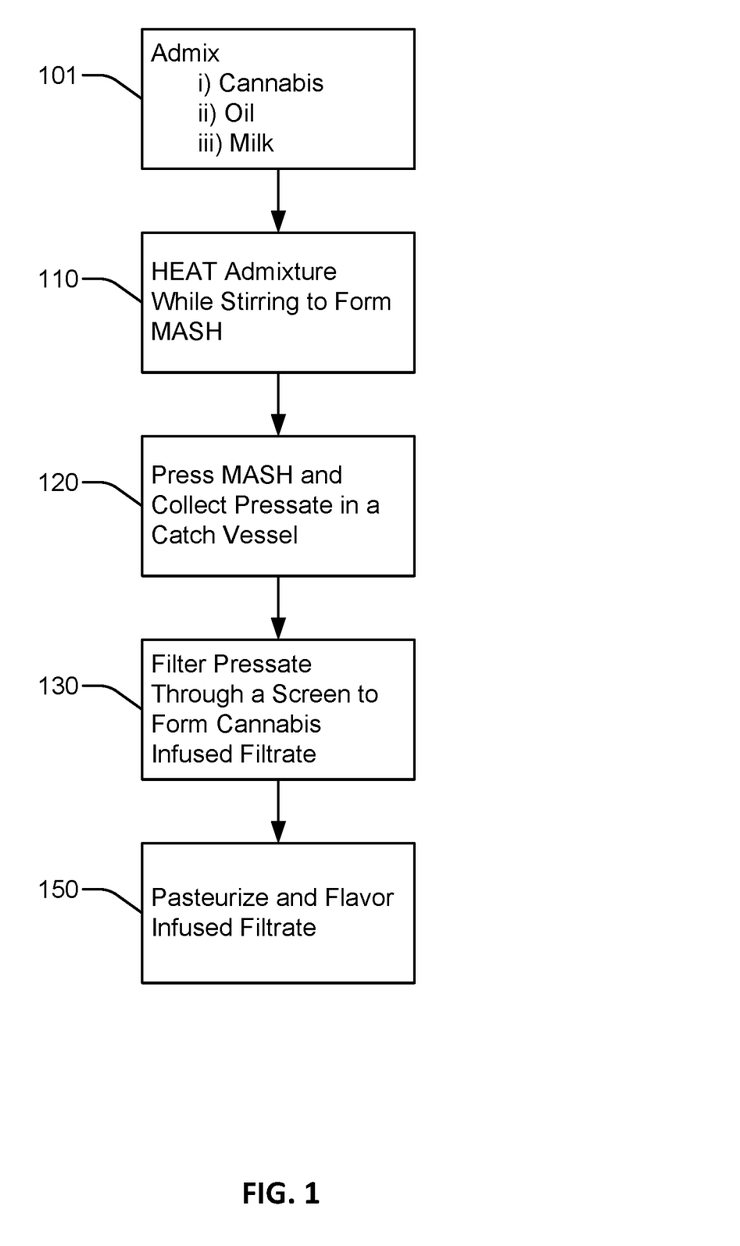
FIG. 1 provides a brief description of one embodiment of the inventive process.

FIG. 1 is a flow diagram of an embodiment of the method of the present invention. In step 101, the ingredients *cannabis*, oil, and a milk are combined to form an admixture.

In certain embodiments, the ingredients are added to a kettle, such as a brew kettle. In certain embodiments, the *cannabis* is added to the kettle first, followed by the oil and milk. However, a skilled artisan will appreciate that the components can be added in any order, including simultaneously.

In certain embodiments, the *cannabis* is freshly harvested *Cannabis* plant material. In certain embodiments, the *cannabis* is preserved *Cannabis* plant material.

In certain embodiments, the *cannabis* is raw *cannabis*. Raw *cannabis* is *Cannabis* plant material that has been harvested, vacuum-sealed (e.g., into food-grade bags), and then immediately frozen. The *cannabis* can be stored frozen and under vacuum, then used in the methods herein.

In certain embodiments, the *cannabis* is a block that is cut into strips to be more easily extracted. For example, an about 5 lb block of *cannabis* can be cut into about 6, 7, 8, 9, or 10 strips (e.g., 8 strips/5 lb, or about 0.6 to 0.65 lb strips). A knife or other sharp bladed instrument can be used to cut the *cannabis* into strips.

A variety of oils can be used. In certain embodiments, a vegetable oil is used, such as coconut oil. In certain embodiments, the oil is selected from safflower, corn, olive, coconut, peanut, sunflower, cottonseed, palm, rapeseed, soybean, or sesame oil. In certain embodiments, cocoa butter is used.

In certain embodiments, a nut oil is used. In certain embodiments, a seed oil is used. In certain embodiments, the oil is selected from hemp seed, flax seed, pumpkin seed, sesame seed, china seed, sunflower seed, soy, almond, cashew, hazelnut, walnut, and peanut oil. In certain embodiments, the oil is selected from beech, Brazil nut, chestnut, pecan, kola nut, macadamia, and pistachio. In certain embodiments, hemp oil is used.

In certain embodiments, a mixture of oils is used. This may be a mixture of oils of the same type (e.g., hemp oil and a second seed oil) or of different types (e.g., a nut oil and a vegetable oil).

In certain embodiments, about 1 to 10 ounces of oil is used per pound of *cannabis*. For example, about 1, 1.25, 1.5, 1.75, 2, 2.25, 2.5, 3, 3.5, 4, 4.5, 5, 5.5, 6, 6.5, 7, 7.5, 8, 8.5, 9, 9.5, or 10 ounces of oil can be used per pound of *cannabis*. In certain embodiments, about 2 to 7, 3 to 7, 2 to 6, 2 to 5, 3 to 5, 3 to 6, 4 to 6, or 4 to 7 ounces are used in the methods herein.

A variety of milks can be used. Suitable sources of milk include, but are not limited to, cow, goat, sheep, camel, horse, donkey, yak, reindeer, hemp seed, flax seed, pumpkin seed sesame seed, china seed, sunflower seed, coconut, soy, almond, cashew, rice, *quinoa*, barley, spelt, oat, hazelnut, walnut, peanut, lupine, and pea.

In certain aspects, the milk used does not include lactose. In certain aspects, the milk used is selected from almond, cashew, coconut, flax, hazelnut, hemp, macadamia, oat, rice, and soy. In certain aspects, the milk used is selected from almond, rice, coconut, flax, and hemp. In certain aspects, hemp seed milk is used.

In certain embodiments, about 1 to 5 quarts of milk is used per pound of *cannabis*. For example, about 1, 1.5, 2, 2.5, 3, 3.5, 4, 4.5, or 5 quarts/lb is used. In some embodiments, about 1 to 3, 1 to 4, 2 to 5, 2 to 4, or 3 to 5 quarts of milk is used per pound of *cannabis*. A more viscous *cannabis* milk can be produced using less milk. A less viscous *cannabis* milk can be produced using more milk.

As described in step 110, the admixture is heated. The temperature of the admixture in the brew kettle can be about 100° F. to about 230° F., about 150° F. to about 220° F., or even about 190° F. to about 210° F. (e.g., about 180, 183, 185, 187, 190, 193, 195, 198, 200, 203, 205, 208, or 210° F.). In certain aspects, the temperature is about 200° F. or about 205° F., such as 200° F. (e.g., 198, 199, 200, 201, 202, 203, 204, 205, 206 or 207° F.). In a preferred aspect, the admixture is stirred with an overhead stirrer while being heated.

In some embodiments, the pre-mash mixture is heated to about 200° F. (e.g., about 187, 190, 193, 195, 198, 200, 203, 205, 208, or 210° F.). In some embodiments, the pre-mash mixture is stirred in the same direction during heating. In some embodiments, the pre-mash mixture is heated multiple times (e.g., at least twice) before the pressing.

In certain embodiments, the heating and stirring can be performed in about 10-20 minutes for each heating and mixing cycle (e.g., about 8, 9 10, 11, 12, 13, 14, 15, 16, 17, 18, 19, 20, 21, 22, 23, 24, or 25 minutes). In certain embodiments, the stirring and heating can be done in various cycles. There can be multiple cycles. For example, there can be 1-10 heating cycles and cooling cycles, such as 1, 2, 3, 4, 5, 6, 7, 8, 9, or 10 heating or cooling cycles. In certain embodiments, the admixture is allowed to cool between heating cycles. In certain embodiments, the cooling of the admixture produces a mash.

Figure 2A:
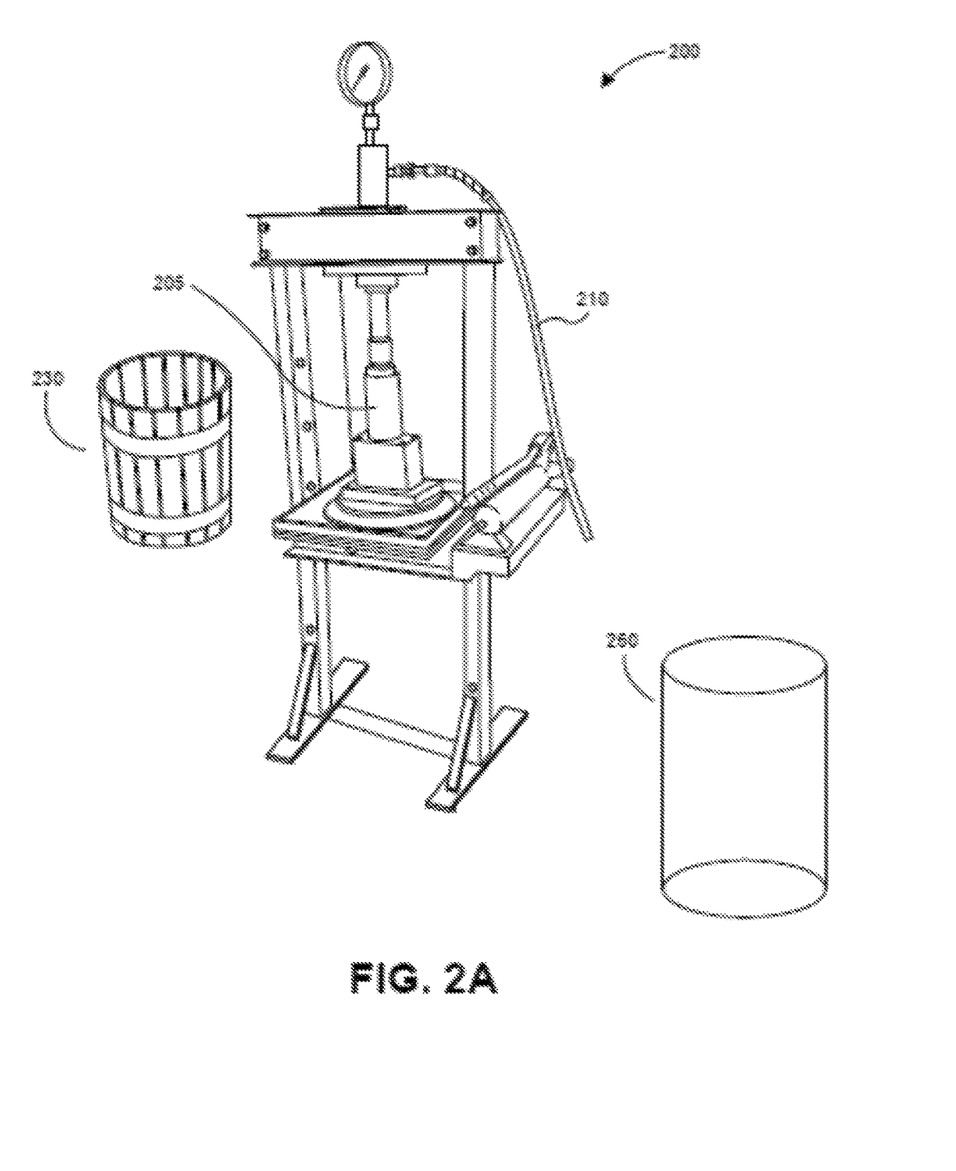
FIG. 2A provides a drawing of a press (200) that can be used for conducting the inventive process. In the embodiment shown, the press includes a piston to press the mash (205), a pressure line to drive the piston (210), a pressing vessel for the mash (230, shown outside of the press), and a collection vessel (260, shown outside of the press).
Figure 2B:
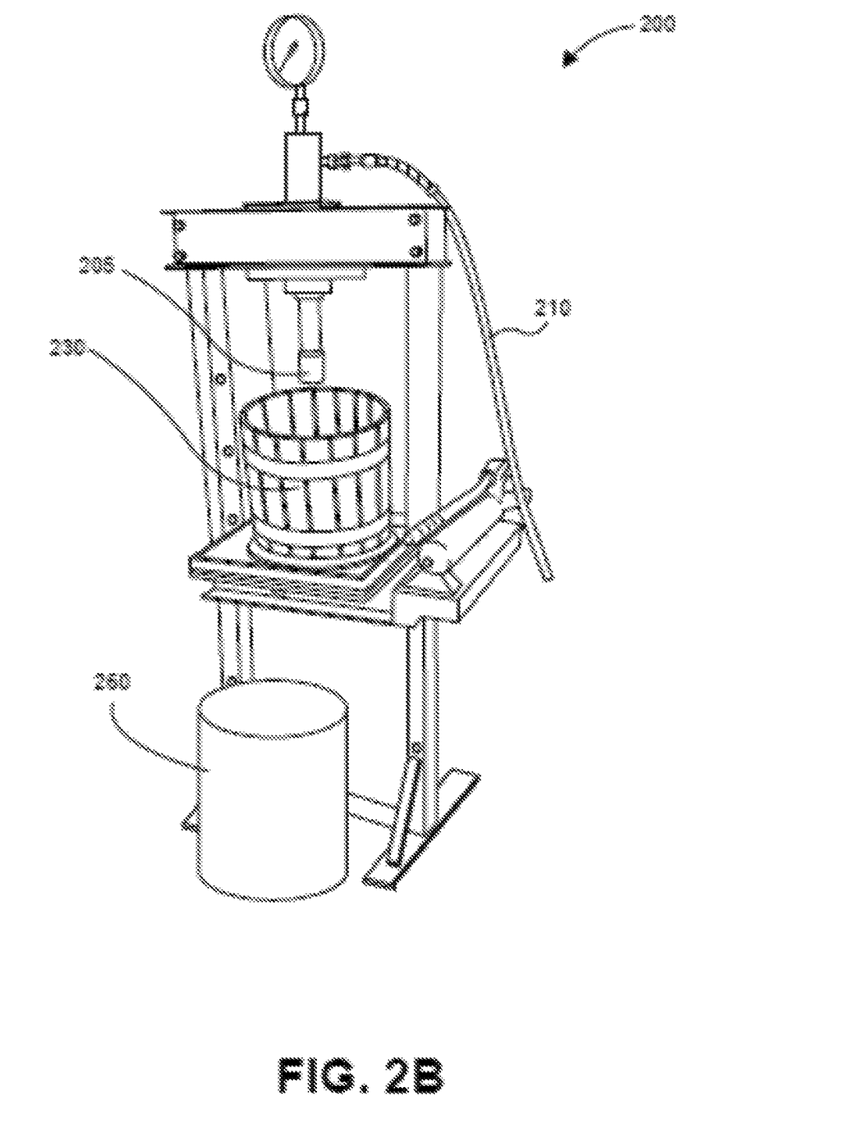
FIG. 2B provides an illustration of the press (200), including a piston (205), a pressure line (210), sample pressing vessel (230) shown in the press, and a collection vessel (260).

Next, as shown in step 120, the mash is pressed to yield a pressate. In certain preferred embodiments, an agricultural press is used. FIG. 2 is one example of a press suitable to press the mash to form the pressate. The pressate can be collected into a vessel such as a catch vessel.

FIG. 2A provides a drawing of a press 200 that can be used for conducting the inventive process. The press includes a piston to press the mash 205, a pressure line to drive the piston 210, a pressing vessel for the mash 230, shown outside of the press, and a collection vessel 260, shown outside of the press. In operation, the pressing vessel 230 is underneath the piston 205 and the collection vessel 260 is between the legs of the press.

Figure 3A:
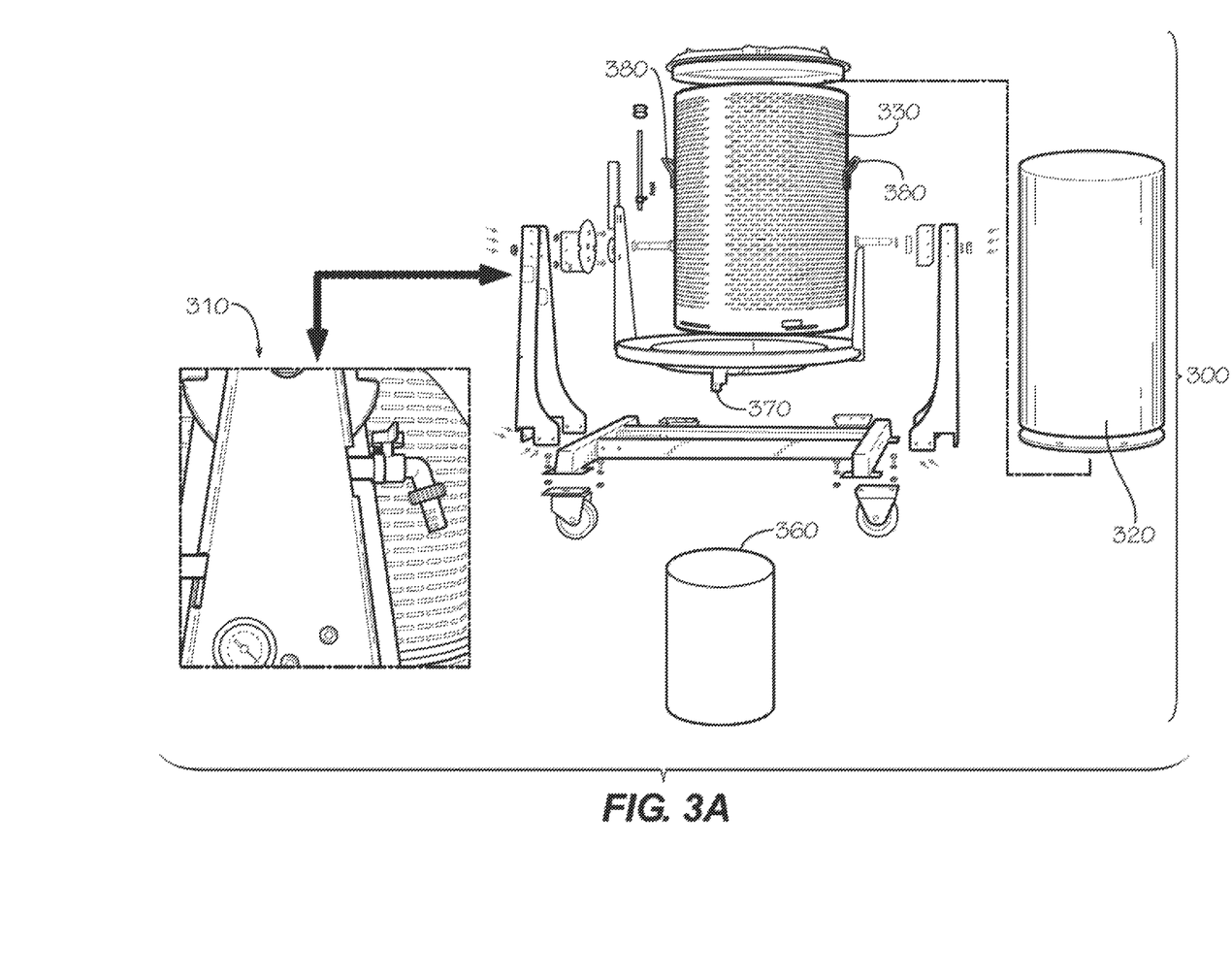
FIG. 3A provides a drawing of an alternative press (300) that can be used for conducting the inventive process. In the embodiment shown, the press includes a bladder to press the mash (320), a support member with a pressure line to drive the bladder (310), a pressing vessel for the mash (330), a collection vessel (360, shown outside of the press), a exit point for the pressate (370), and handles for the pressing vessel (380).

FIG. 3A provides a drawing of a press 300 that can be used for conducting the inventive process. The press includes a bladder 320 to press the mash, a support member with a pressure line to drive the bladder 310, a pressing vessel 330 for the mash, with the vessel shown outside of the press, and a collection vessel 360, shown outside of the press. In operation, the pressing vessel 330 is surrounding the bladder 320 and the collection vessel 360 is between the legs of the press.

In some embodiments, the pressing is through a nylon mesh. In some embodiments, the pressate is filtered through a screen (e.g., an about 220 micron screen).

As shown in step 130, the pressate is filtered through a screen to form a *cannabis*-infused filtrate. Typical screens include about a 180-250 micron screen, about 190-230. or about 200-220 micron screens. After screening, the filtrate is clear of particulates.

In step 150, the filtrate is pasteurized and optionally flavored. Suitable flavors include, but are not limited to, chocolate, vanilla, strawberry, mocha, peppermint, black cherry, coffee and the like. The method produces a *cannabis*-infused milk.

In certain embodiments, the present invention provides a pharmaceutical composition, the composition comprising: a *cannabis*-infused milk; and a flavoring.

The *cannabis*-infused milk of the present invention comprises $\Delta^9$-tetrahydrocannabinol (THC). In certain embodiments, the *cannabis*-infused milk is about 0.1% to about 30% THC w/w. In certain embodiments, the THC content is about 1-5%, or about 5-25%, or about 7-18%, or about 8-14% THC w/w. In certain embodiments, the THC of the *cannabis*-infused milk is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3. 2.5, 2.8, 3.0, 3.3, 3.5, 3.8, 4.0, 4.5, 5.0, 5.5, 6.0, 6.5, 7.0, 7.5, 8, 9, 10, 11, 12, 13, 14, 15, 16, 17, 18, 19, 20, 21, 22, 23, 24, 25, 26, 27, 28, 29, or about 30% w/w THC.

In certain other embodiments, the *cannabis*-infused milk can be more concentrated and the THC content can be higher, such as about 30% to about 50% THC w/w (e.g., about 30, 31, 32, 33, 34, 35, 36, 37, 38, 39, 40, 41, 42, 43, 44, 45, 46, 47, 48, 49, or 50% w/w THC).

The *cannabis*-infused milk of the present invention comprises cannabinoids. In certain embodiments, the *cannabis*-infused milk is about 0.1% to about 30% w/w in its total concentration of cannabinoids. In other embodiments, the total concentration of cannabinoids is about 0.1%-1.0%, about 0.01%-0.5%, or about 0.5-2.5%, or about 0.3-0.8%, or about 0.8-1.4% w/w. In other embodiments, the total concentration of cannabinoids is about 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.75, 0.8, 0.85, 0.9, 0.95, 1.0, 1.1, 1.2, 1.3, 1.4, 1.5, 1.6, 1.7, 1.8, 1.9, or about 2.0% w/w.

In certain embodiments, the *cannabis*-infused milk is about 0.1% to about 30% w/w total concentration of cannabinoids. In other embodiments, the total concentration of cannabinoids is about 1%-5%, or about 5-25%, or about 7-18%, or about 8-14% w/w. In other embodiments, the total concentration of cannabinoids is about 1, 2, 3, 4, 5, 6, 7, 8, 9, 10, 11, 12, 13, 14, 15, 16, 17, 18, 19, or about 20% w/w.

In still other embodiments, the *cannabis*-infused milk can be more concentrated and the total concentration of cannabinoids can be higher, such as about 30% to about 50% w/w.

The *cannabis*-infused milk of the present invention comprises $\Delta^9$-tetrahydrocannabinol ($\Delta^9$-THC). In certain embodiments, the *cannabis*-infused milk is about 0.01% to about 30% $\Delta^9$-THC w/w. In other embodiments, the $\Delta^9$-THC content is about 0.01%-1.0%, about 0.01%-0.5%, or about 0.5-2.5%, or about 0.3-0.8%, or about 0.8-1.4% $\Delta^9$-THC w/w. In other embodiments, the $\Delta^9$-THC of the *cannabis*-infused milk is about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, or about 2.0% w/w $\Delta^9$-THC.

In certain embodiments, the *cannabis*-infused milk is about 0.1% to about 30% $\Delta^9$-THC w/w. In other embodiments, the $\Delta^9$-THC content is about 1%-5%, or about 5-25%, or about 7-18%, or about 8-14% $\Delta^9$-THC w/w. In other embodiments, the $\Delta^9$-THC of the *cannabis*-infused milk is about 1, 2, 3, 4, 5, 6, 7, 8, 9, 10, 11, 12, 13, 14, 15, 16, 17, 18, 19, or about 20% w/w $\Delta^9$-THC.

In still other embodiments, the *cannabis*-infused milk can be more concentrated and the $\Delta^9$-THC content can be higher, such as about 30% to about 50% $\Delta^9$-THC w/w.

In certain embodiments, the *cannabis*-infused milk of the present invention comprises cannabidiol (CBD). In certain embodiments, the *cannabis*-infused milk is about 0.01% to about 25% CBD w/w. In other embodiments, the CBD content is about 0.01%-1.0%, about 0.01%-0.5%, about 0.1-2.5%, about 0.3-0.8%, or about 0.8-1.4% CBD w/w. In other embodiments, the CBD of the *cannabis*-infused milk is about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, or about 2.0% w/w CBD.

In certain embodiments, the *cannabis*-infused milk is about 1% to about 25% CBD w/w. In other embodiments, the CBD content is about 1%-5%, or about 5-25%, or about 7-18%, or about 8-14% CBD w/w. In other embodiments, the CBD of the *cannabis*-infused milk is about 1, 2, 3, 4, 5, 6, 7, 8, 9, 10, 11, 12, 13, 14, 15, 16, 17, 18, 19, 20, 21, 22, 23, 24, or about 25% w/w CBD.

In certain embodiments, the *cannabis*-infused milk of the present invention comprises a minor cannabinoid, such as cannabigerol, cannabigerolic acid, cannabidiolic acid, cannabichromene, $\Delta^8$-THC, or 2-COOH-$\Delta^9$-THC. In other embodiments, the content of the minor cannabinoid is about 0.001%-1.0%, about 0.01%-0.5%, or about 0.5-2.5%, or about 0.3-0.8%, or about 0.8-1.4% w/w. In other embodiments, the content of the minor cannabinoid is about 0.001, 0.002, 0.003, 0.004, 0.005, 0.006, 0.007, 0.008, 0.009, 0.010, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, or about 2.0% w/w. In some embodiments, the *cannabis*-infused milk comprises two or more minor cannabinoids, which may be present in the same or different concentrations.

III. Examples

Example 1: General Method

The specific compositions discussed below are prepared by the general method of FIG. 1.

To a brew kettle was added the *cannabis*, oil, and milk as discussed below. The kettle is covered, and the admixture was heated to 200° C., using a high-speed mixer to provide ca. 2 min stirring/10 min. The mixture was allowed to cool. The heating/cooling cycle was repeated twice (3× total).

The cooled mash was transferred from the brew kettle to the press. The mash was pressed through a nylon mesh bag within a slotted barrel with a catch pot underneath (e.g., FIG. 2B).

The pressate was transferred from the catch pot to a filtering bag within a large pot and then gravity filtered through a 220 micron screen. The filtrate was collected in a pasteurization/flavoring pot.

The filtered, *cannabis*-infused milk was pasteurized and flavored in the pot while being continuously stirred in the same direction.

Example 2: General Method II

The specific compositions discussed below are prepared by the general method of FIG. 1.

To a brew kettle was added the *cannabis*, oil, and milk as discussed below. The kettle is covered, and the admixture was heated to 200° C., using a high-speed mixer to provide ca. 2 min stirring/10 min. The mixture was allowed to cool. The heating/cooling cycle was repeated twice (3× total).

Figure 3B:
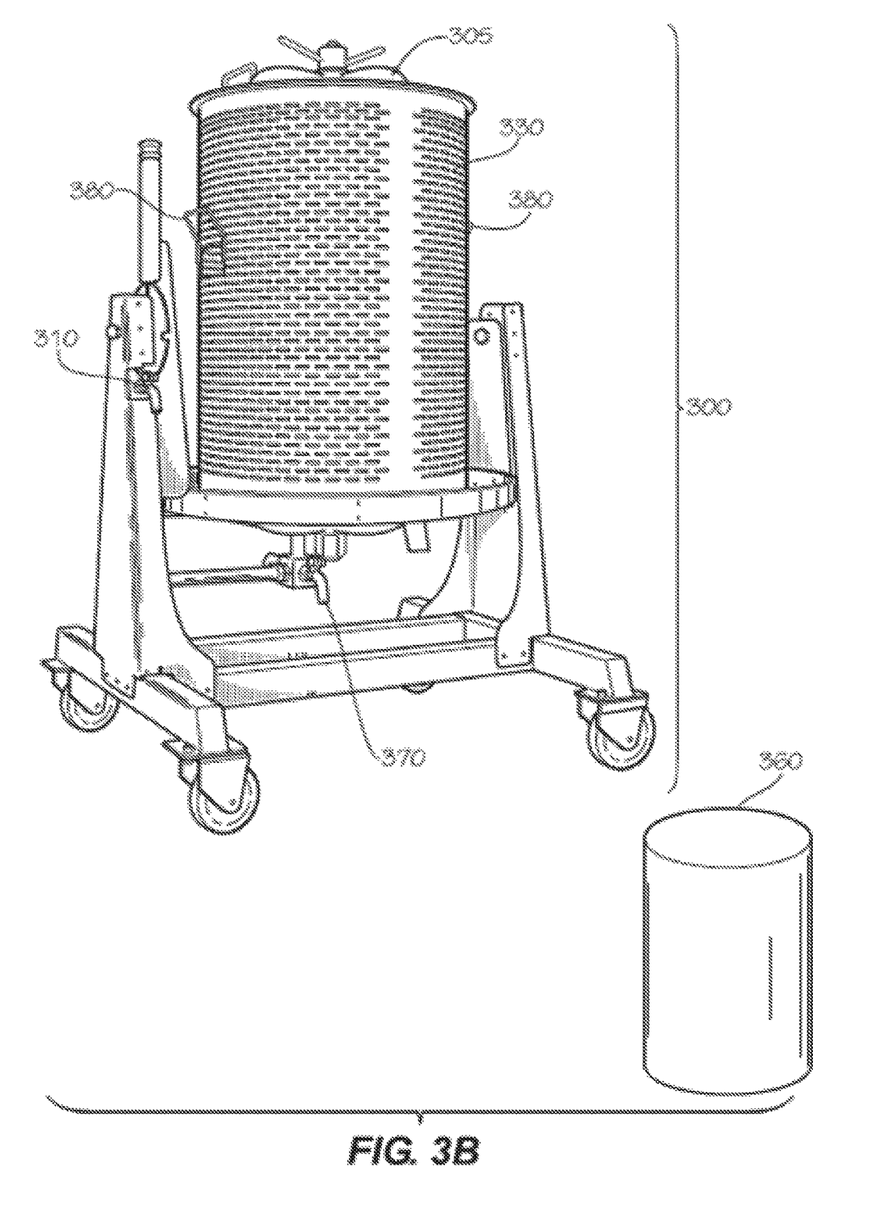
FIG. 3B provides an illustration of the alternative press (300), including a vessel top (305), a support member with a pressure line (310), a sample pressing vessel (330), collection vessel (360), a exit point for the pressate (370), and handles for the pressing vessel (380).

The cooled mash was transferred from the brew kettle to the press. The mash was pressed through a nylon mesh bag within a slotted barrel with a catch pot underneath (e.g., FIG. 3B).

The pressate was transferred from the catch pot to a filtering bag within a large pot and then gravity filtered through a 220 micron screen. The filtrate was collected in a pasteurization/flavoring pot.

The filtered, *cannabis*-infused milk was pasteurized and flavored in the pot while being continuously stirred in the same direction.

Example 3: THC Chocolate Hemp Milk Formulation

The components listed below were used in the procedure of Example 1 or 2.

| | |
|---|---|
| 64 quarts hemp milk | 25 lbs. raw cannabis |
| 78 oz. virgin coconut oil | 11.25 liters chocolate syrup |
| 0.75 liters vanilla syrup | |

The method provided a pharmaceutical composition comprising a *cannabis*-infused milk.

Example 4: THC Vanilla Hemp Milk Formulation

The components listed below were used in the procedure of Example 1 or 2.

| | |
|---|---|
| 64 quarts hemp milk | 25 lbs. raw cannabis |
| 78 oz. virgin coconut oil | 2 liters vanilla extract |
| 12 liters vanilla syrup | |

The method provided a pharmaceutical composition comprising a *cannabis*-infused milk.

Example 5: THC Strawberry Hemp Milk Formulation

The components listed below were used in the procedure of Example 1 or 2.

| | |
|---|---|
| 64 quarts hemp milk | 25 lbs. raw cannabis |
| 78 oz. virgin coconut oil | 64 oz. strawberry extract |
| 11.25 liters strawberry syrup | 0.75 liters vanilla syrup |

The method provided a pharmaceutical composition comprising a *cannabis*-infused milk.

Example 6: THC Mocha Hemp Milk Formulation

The components listed below were used in the procedure of Example 1 or 2.

| | |
|---|---|
| 64 quarts hemp milk | 30 lbs. raw cannabis |
| 78 oz. virgin coconut oil | 8.25 liters espresso syrup |
| 8.25 liters chocolate syrup | 6 liters espresso extract |
| 0.75 liters vanilla syrup | |

The method provided a pharmaceutical composition comprising a *cannabis*-infused milk.

Example 7: THC Peppermint Chocolate Hemp Milk Formulation

The components listed below were used in the procedure of Example 1 or 2.

| | |
|---|---|
| 64 quarts hemp milk | 25 lbs. raw cannabis |
| 78 oz. virgin coconut oil | 0.75 liters peppermint extract |
| 11.25 liters chocolate syrup | 0.25 liters vanilla syrup |

The method provided a pharmaceutical composition comprising a *cannabis*-infused milk.

Example 8: High CBD Pumpkin Hemp Formulation

The components listed below were used in the procedure of Example 1 or 2.

| | |
|---|---|
| 64 quarts hemp milk | 10 lbs. raw cannabis |
| 78 oz. virgin coconut oil | 64 oz pumpkin pie extract |
| 8 liters pumpkin spice syrup | 6 liters pumpkin pie syrup |
| 1 liter vanilla syrup | |

The method provided a pharmaceutical composition comprising a *cannabis*-infused milk.

Example 9: High CBD Black Cherry Hemp Formulation

The components listed below were used in the procedure of Example 1 or 2.

| | |
|---|---|
| 64 quarts hemp milk | 10 lbs. raw cannabis |
| 78 oz. virgin coconut oil | 24 oz. black cherry extract |
| 11 liters cherry syrup | 2 liters vanilla syrup |

The method provided a pharmaceutical composition comprising a *cannabis*-infused milk.

Example 10: 3:1 High CBD Vanilla Hemp Milk Formulation

The components listed below were used in the procedure of Example 1 or 2.

| | |
|---|---|
| 64 quarts hemp milk | 25 lbs. raw cannabis |
| 78 oz. virgin coconut oil | 2 liters vanilla extract |
| 12 liters vanilla syrup | |

The method provided a pharmaceutical composition comprising a *cannabis*-infused milk.

Example 11: 1:1 High CBD Vanilla Hemp Milk Formulation

The components listed below were used in the procedure of Example 1 or 2.

| | |
|---|---|
| 64 quarts hemp milk | 25 lbs. raw cannabis |
| 78 oz. virgin coconut oil | 2 liters vanilla extract |
| 12 liters vanilla syrup | |

The method provided a pharmaceutical composition comprising a *cannabis*-infused milk.

Example 12: 0.17% Cannabinoid Formulation

The method provided a pharmaceutical composition comprising 0.17% w/w total percentage of cannabinoids: 0.03% $\Delta^9$-THC, 0.02% THCA (2-COOH-$\Delta^9$-THC), 0.04% CBD, and 0.08% CBDA (cannabidiolic acid).

Example 13: 0.31% Cannabinoid Formulation

The method provided a pharmaceutical composition comprising 0.31% w/w total percentage of cannabinoids: 0.24% $\Delta^9$-THC, 0.06% THCA (2-COOH-$\Delta^9$-THC), 0.01% cannabichromene (CBC), and 0.01% cannabigerol (CBG).

Example 14: 0.54% Cannabinoid Formulation

The method provided a pharmaceutical composition comprising 0.54% w/w total percentage of cannabinoids: 0.41% $\Delta^9$-THC, 0.11% THCA, 0.01% cannabigerol (CBG), and 0.01% cannabigerolic acid (CBGA).

It is understood that the examples and embodiments described herein are for illustrative purposes only. Various modifications or changes in light thereof will be suggested to persons skilled in the art and are to be included within the spirit and purview of this application and the scope of the appended claims. All publications, patents, and patent applications cited herein are hereby incorporated by reference in their entirety for all purposes.

What is claimed is:

1. A method for preparing a *cannabis*-infused milk, wherein the method consists essentially of:
   heating a mixture of *cannabis*, a milk, and coconut oil to a temperature from 150° F. to 220° F. to form a mash;
   pressing the mash to form a pressate; and
   filtering the pressate to produce the *cannabis*-infused milk.

2. The method of claim 1, wherein the *cannabis*-infused milk is pasteurized.

3. The method of claim 1, wherein the *cannabis*-infused milk is flavored.

4. The method of claim 1, wherein the *cannabis* is raw *cannabis*.

5. The method of claim 1, wherein the milk does not contain lactose.

6. The method of claim 5, wherein the milk is almond, rice, coconut, flax, or hemp milk.

7. The method of claim 6, wherein the milk is hemp milk.

8. The method of claim 1, wherein the mixture is heated to about 200° F.

9. The method of claim 1, wherein the mixture is heated at least twice before the pressing.

10. The method of claim 1, wherein the pressing is through a nylon mesh.

11. The method of claim 1, wherein the pressate is filtered through a screen.

12. The method of claim 11, wherein the screen is an about 220 micron screen.

* * * * *